United States Patent
Roberts (10) Patent No.: US 11,065,473 B2
(45) Date of Patent: Jul. 20, 2021

(54) METHODS AND SYSTEMS FOR CHECKING ALIGNMENT OF COMPONENTS OF A RADIOTHERAPY SYSTEM

(71) Applicant: Elekta Limited, Crawley (GB)

(72) Inventor: David Anthony Roberts, East Grinstead (GB)

(73) Assignee: Elekta Limited, Crawley (GB)

( * ) Notice: Subject to any disclaimer, the term of this patent is extended or adjusted under 35 U.S.C. 154(b) by 422 days.

(21) Appl. No.: 16/196,658

(22) Filed: Nov. 20, 2018

(65) Prior Publication Data

US 2019/0151683 A1 May 23, 2019

(51) Int. Cl.
*A61N 5/10* (2006.01)

(52) U.S. Cl.
CPC ......... *A61N 5/1049* (2013.01); *A61N 5/1045* (2013.01); *A61N 5/1075* (2013.01); *A61N 5/1077* (2013.01); *A61N 5/107* (2013.01); *A61N 5/1039* (2013.01); *A61N 2005/1052* (2013.01); *A61N 2005/1054* (2013.01); *A61N 2005/1055* (2013.01); *A61N 2005/1087* (2013.01)

(58) Field of Classification Search
CPC .. A61N 5/1049; A61N 5/1045; A61N 5/1077; A61N 5/1075; A61N 5/1039; A61N 5/107; A61N 2005/1054; A61N 2005/1052; A61N 2005/1087; A61N 2005/1055

See application file for complete search history.

(56) References Cited

U.S. PATENT DOCUMENTS

| 7,668,292 B1 * | 2/2010 | Bose ................... A61N 5/1049 378/65 |
| 2009/0013468 A1 | 1/2009 | Bourne et al. |
| 2016/0114190 A1 | 4/2016 | Brown et al. |

OTHER PUBLICATIONS

Search Report from corresponding GB Application No. 1719298.0 dated May 2, 2018 (4 pages).

* cited by examiner

*Primary Examiner* — Boniface N Nganga
(74) *Attorney, Agent, or Firm* — Finnegan, Henderson, Farabow, Garrett & Dunner LLP (57) ABSTRACT

A method of operating a radiotherapy system mounted on a gantry surrounding a magnetic resonance imaging system is provided, the radiotherapy system comprising a radiotherapy beam generator, and a radiotherapy imaging system, wherein the gantry is arranged to rotate the radiotherapy beam generator around the magnetic resonance imaging system. The method comprises obtaining a reference image, the reference image including a predetermined feature of the magnetic resonance imaging system located near the radiotherapy imaging system; rotating the gantry relative the magnetic resonance imaging system; obtaining a second image, the second image including the predetermined feature of the magnetic resonance imaging system located near the radiotherapy imaging system; and determining changes in the relative positions of the radiotherapy beam generator, the radiotherapy imaging system, and the magnetic resonance imaging system based on differences in the position of the predetermined feature in the reference image and in the further image.

20 Claims, 4 Drawing Sheets

METHODS AND SYSTEMS FOR CHECKING ALIGNMENT OF COMPONENTS OF A RADIOTHERAPY SYSTEM

CROSS-REFERENCE TO RELATED PATENT APPLICATIONS

This application claims the benefit of priority to United Kingdom Application No. GB 1719298.0, filed Nov. 21, 2017, which is hereby incorporated by reference in its entirety.

FIELD OF THE INVENTION

The exemplary embodiments of the present disclosure relate to systems and methods for checking radiotherapeutic beam alignment in radiation therapy apparatus. While the embodiments of the present disclosure may be applied in various types of radiotherapy systems, it is particularly, but not exclusively, useful in image-guided radiotherapy systems, including a linear accelerator source and a magnetic resonance imaging (MRI) system.

BACKGROUND ART

Radiotherapeutic apparatus is well-known, and consists of a source of radiation which emits a beam of radiation that is directed toward a patient in order to destroy or otherwise harm cancerous cells within the patient. Usually, the beam is collimated in order to limit its spatial extent to a desired region within the patient, usually the tumour or a sub-section of the tumour, and to avoid irradiating nearby healthy and/or sensitive tissue. The source can be a linear accelerator for high-energy (MV) X-radiation, or an isotopic source such as Co-60. The source is often mounted on a rotatable gantry, so as to be rotated around the patient in order to irradiate the desired region from a number of different directions, thereby reducing the dose applied to healthy tissue around the desired region. The collimator can move to change the shape of the beam as the source rotates, in order to build up a complex dose distribution for tumours with more challenging shapes and/or which are located near to sensitive areas. An electronic portal imaging device (EPID) may be mounted to the gantry on the opposite side to the source so as to receive the beam once it has been attenuated by passage through the patient; this device produces an image which can be used for correctly aligning or calibrating the system, as well as for assessing the patient's location and the placement of the radiotherapeutic treatment.

Incorporating real-time image guidance into radiotherapy can improve tumour targeting accuracy, enabling better avoidance of critical structures and reducing side effects. Such guidance is of particular benefit if a non-ionizing imaging technique such as MRI (magnetic resonance imaging) is employed. Work is currently being undertaken to integrate a linear accelerator with an MR scanner; integrating high-quality MRI with a linear accelerator (creating a "MR Linac", or MRL) allows tissue to be tracked online, and therapeutic radiation beams can be guided to their targets (which may be moving and deforming, such as when the patient breathes) with sub-millimetre precision during treatment.

US 2016/0114190 proposes a method to calibrate the alignment of the source and MR scanner using a phantom, which is placed in the system at the location of the treatment zone, so that the isocentre of the treatment beam is properly aligned with the MR scanner image. However, because the components of the radiotherapy system are mounted on a moveable gantry, it is possible that alignment errors can be introduced following movement of the gantry after calibration. Repeated use of phantoms is not practical due to the time taken to conduct beam alignment. During normal use, there is little information as to whether or not changes in alignment have occurred that require a re-alignment of the system components.

The embodiments of the present disclosure aim to enable identification of relative movement of the components of the system, and potential identification of the specific components that may have moved.

SUMMARY OF THE INVENTION

One exemplary embodiment of the present disclosure provides a method of operating a radiotherapy system comprising a gantry that is rotatable around a treatment location; a radiotherapy beam generator located on the gantry; a radiotherapy imaging system located on the opposite side of the treatment location; and at least one component that is static with respect to the treatment location; wherein a beam path is defined between the radiotherapy beam generator and the radiotherapy imaging system so as to pass through the static component; the method comprising obtaining a reference image using the radiotherapy imaging system with the gantry in a predetermined position so as to provide the beam generator, the imaging system and the static component in reference positions, the reference image including the static component; rotating the gantry relative to the static component; returning the gantry to the predetermined position; obtaining a second image using the radiotherapy imaging system with the gantry in the predetermined position, the second image including the static component; and determining changes in the relative positions of the radiotherapy beam generator, the radiotherapy imaging system, and the static component based on differences in the position of the static component in the reference image and in the second image.

In certain embodiments, the gantry may surround a magnetic resonance imaging system, wherein the at least one component that is static with respect to the treatment location may be a predetermined feature of the magnetic resonance imaging system, such that the radiotherapy beam generator can be located on one side of the magnetic resonance imaging system; the radiotherapy imaging system can be located on the opposite side of the magnetic resonance imaging system; the beam path can be defined between the radiotherapy beam generator and the radiotherapy imaging system so as to pass through the magnetic resonance imaging system; and the gantry may be configured or arranged to rotate the radiotherapy system around the magnetic resonance imaging system; the method comprising: obtaining the reference image using the radiotherapy imaging system, the reference image including the predetermined feature of the magnetic resonance imaging system located near the radiotherapy imaging system; rotating the radiotherapy system relative to the magnetic resonance imaging system; obtaining the further image using the radiotherapy imaging system, the further image including the predetermined feature of the magnetic resonance imaging system located near the radiotherapy imaging system; and determining changes in the relative positions of the radiotherapy beam generator, the radiotherapy imaging system, and the magnetic resonance imaging system from differences in the position of the predetermined feature in the reference image and in the further image.

Because the MRI system is essentially static, changes in the position of the features of the MRI system in the image may be primarily due to changes in relative position of the components of the radiotherapy system, including changes within components, such as within the beam generator.

The method can further comprise, following the step of rotating the radiotherapy system relative to the magnetic resonance imaging system:
- determining a degree of rotation to rotate the gantry to the position in which the reference image was obtained;
- providing a control signal for the gantry to rotate through the degree of rotation;
- obtaining the reference image; and
- determining an error in the rotational position of the gantry from changes in the relative position of the predetermined feature in the reference and further images.

The predetermined feature can include part of a cryostat and/or part of a coil support of the magnetic resonance imaging system.

The beam path can extend through a gap provided in the cryostat and/or the coil support, and the predetermined feature in the reference image in this case can include the edges of the gap.

The reference image may include features of a collimation system, such as one or more leaves of a multi leaf collimator, located between the beam generator and the radiotherapy imaging system.

The predetermined feature in the reference image can include both the edges of the gap and features of the collimation system.

Another embodiment of the present disclosure provides a radiotherapy system comprising a gantry that is rotatable around a treatment location; a radiotherapy beam generator located on the gantry; a radiotherapy imaging system located on the opposite side of the treatment location; and at least one component that is static with respect to the treatment location; wherein a beam path is defined between the radiotherapy beam generator and the radiotherapy imaging system so as to pass through the static component; the system being configured to perform the method according to the first aspect of the invention.

In certain embodiments, wherein the system further comprises a magnetic resonance imaging system, the gantry surrounding the magnetic resonance imaging system, the system comprises the radiotherapy beam generator located on one side of the magnetic resonance imaging system; and the radiotherapy imaging system located on the opposite side of the magnetic resonance imaging system; wherein the beam path is defined between the radiotherapy beam generator and the radiotherapy imaging system so as to pass through the magnetic resonance imaging system; and wherein the gantry is arranged to rotate the radiotherapy beam generator around the magnetic resonance imaging system.

A still further embodiment of the present disclosure provides a non-transitory computer-readable medium storing instructions, which when executed by at least one processor, cause the at least one processor to perform the method, in accordance with the embodiments of the present disclosure.

BRIEF DESCRIPTION OF THE DRAWINGS

The invention will now be described by way of example and with reference to the accompanying figures in which.

DETAILED DESCRIPTION OF THE EMBODIMENTS

Figure 1:
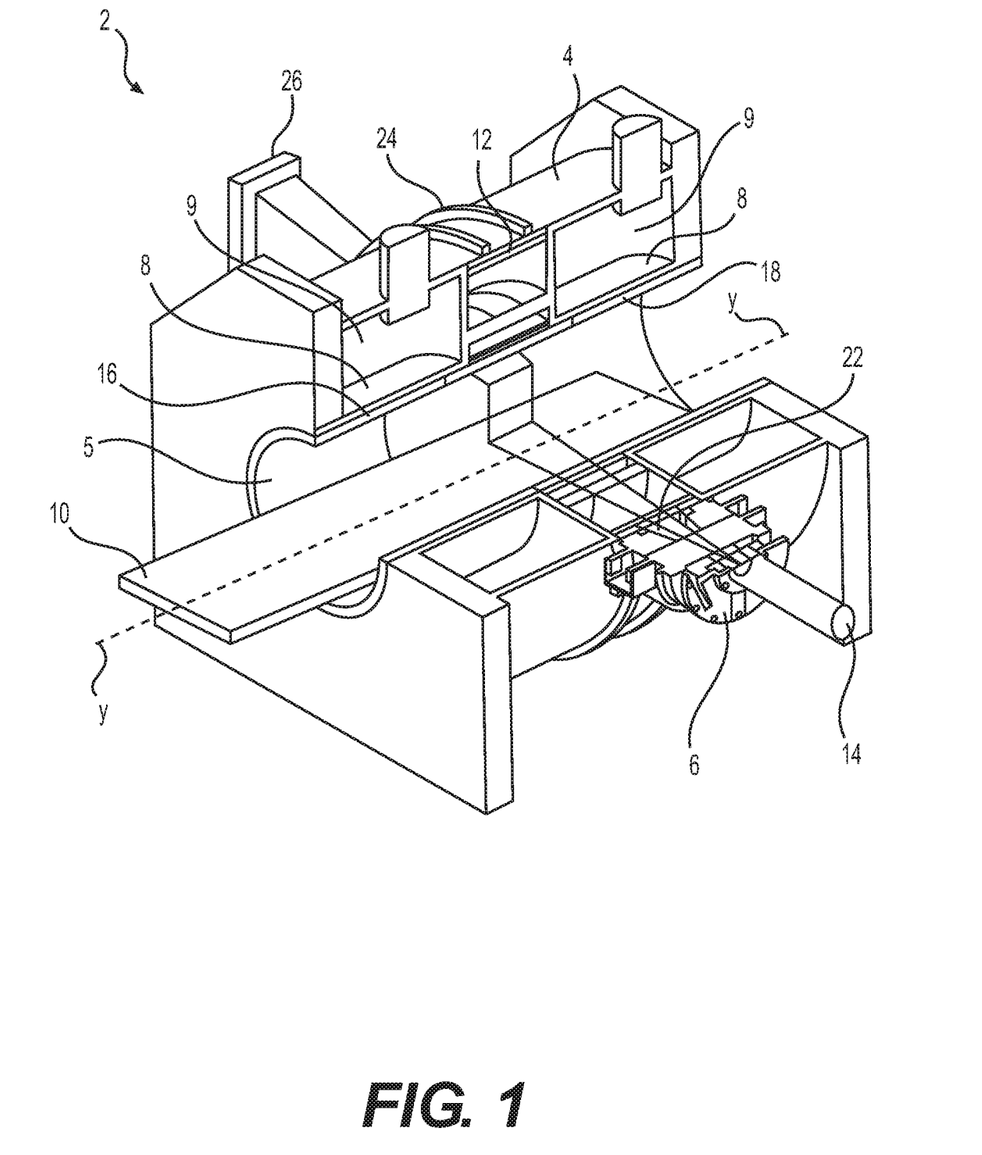
FIG. 1 is a schematic view, in partial cross-section, of an MRI-guided radiotherapy system.

FIG. 1 shows a system 2 comprising a radiotherapy apparatus 6 and a magnetic resonance imaging (MRI) apparatus 4. The system may include a couch 10, for supporting a patient in the apparatus. The couch 10 may be movable along a horizontal, translation axis (labelled "Y"), such that a patient resting on the couch is moved into the bore 5 of the MRI apparatus 4 and into the path of the radiotherapy apparatus 6. In one embodiment, the couch 10 may be rotatable around a central vertical axis of rotation, transverse to the translation axis, although this is not illustrated. The couch 10 may form a cantilever section that projects away from a support structure (not illustrated). In one embodiment, the couch 10 may be moved along the translation axis relative to the support structure in order to form the cantilever section, i.e. the cantilever section may increase in length as the couch is moved and the lift remains stationary. In another embodiment, both the support structure and the couch 10 may move along the translation axis, such that the cantilever section remains substantially constant in length, as described in our US 2009/0013468.

As mentioned above, the system 2 may also comprise an MRI apparatus 4, for producing near real-time imaging of a patient positioned on the couch 10. The MRI apparatus may include a primary magnet 8 which acts to generate the so-called "primary" magnetic field for magnetic resonance imaging. That is, the magnetic field lines generated by operation of the magnet 8 may run substantially parallel to the central translation axis Y. The primary magnet 8 may consist of one or more coils with an axis that runs parallel to the translation axis Y; though not shown, the coils may be coaxial with the translation axis. The one or more coils may be a single coil or a plurality of coaxial coils of different diameter. As illustrated, the one or more coils in the primary magnet 8 may be spaced such that a central window 12 of the magnet 8 is free of coils. In other embodiments, the coils in the magnet 8 may simply be thin enough that they are substantially transparent to radiation of the wavelength generated by the radiotherapy apparatus. The magnet 8 may further comprise one or more active shielding coils, which generates a magnetic field outside the magnet 8 of approximately equal magnitude and opposite polarity to the external primary magnetic field. The more sensitive parts of the system 2, such as the accelerator 14, are positioned in this region outside the magnet 8 where the magnetic field is cancelled, at least to a first order. The magnet 8 may be surrounded by a liquid helium-filled cryostat 9 that is used to maintain the coils of the magnet 8 in a superconducting state. The chambers of the cryostat 9 may be spaced such that the central window 12 is not obstructed.

The MRI apparatus 4 may further comprise two gradient coils 16, 18, which generate the so-called "gradient" magnetic field that is superposed on the primary magnetic field. These coils 16, 18 may generate a gradient in the resultant magnetic field that allows spatial encoding of the protons so that their position can be determined, for example the gradient coils 16, 18 can be controlled such that the imaging data obtained has a particular orientation. The gradient coils 16, 18 may be positioned around a common central axis with the primary magnet 16, and may be displaced from one another along that central axis. This displacement may create a gap, or window, between the two coils 16, 18. In an embodiment where the primary magnet 8 also comprises a central window between coils, the two windows may be aligned with one another.

An RF system may cause the protons to alter their alignment relative to the magnetic field. When the RF electromagnetic field is turned off, the protons return to the original magnetization alignment. These alignment changes may create a signal which can be detected by scanning. The RF system may include a single coil that both transmits the radio signals and receives the reflected signals, dedicated transmitting and receiving coils, or multi-element phased array coils, for example. Control circuitry may control the operation of the various coils 8, 16, 18 and the RF system, and signal-processing circuitry may receive the output of the RF system, generating therefrom images of the patient supported by the couch 10.

As mentioned above, the system 2 may further comprise a radiotherapy apparatus 6 which may deliver doses of radiation to a patient supported by the couch 10. The majority of the radiotherapy apparatus 6, including at least a source of radiation 14 (e.g. an x-ray source and a linear accelerator) and a multi-leaf collimator (MLC) 22, may be mounted on a chassis (also called a "gantry") 24. The gantry 24 may be continuously rotatable around the couch 10 when it is inserted into the treatment area, powered by one or more chassis motors. In the illustrated embodiment, a radiation detecting and imaging device 26 such as an EPID may also be mounted on the gantry 24 opposite the radiation source 14 and with the rotational axis of the gantry positioned between them. The radiotherapy apparatus 6 may further comprise control circuitry, which (with the RF control circuitry) may be integrated within the system 2 shown in FIG. 1 or remote from it, and controls the radiation source 14, the MLC 22 and the gantry motor.

The radiation source 14 may be positioned to emit a beam of radiation through the window defined by the two gradient coils 16, 18, and also through the window 12 defined in the primary magnet 8. The radiation beam may be a cone beam or a fan beam, for example.

In operation, a patient may be placed on the couch 10 and the couch may be inserted into the treatment area defined by the magnetic coils 16, 18 and the gantry 24. The control circuitry may control the radiation source 14, the MLC 22 and the chassis motor to generate a beam of radiotherapeutic radiation and to deliver radiation to the patient through the window 12 between the coils 16, 18. The chassis motor may be controlled such that the gantry 24 rotates about the patient, meaning the radiation can be delivered from different directions. The MLC 22 may have a plurality of elongate leaves oriented orthogonal to the beam axis; an example is illustrated and described in EP 0314214. The leaves of the MLC 22 may be controlled to move (along the Y-axis in FIG. 1) to take different positions blocking or allowing through some or all of the radiation beam, thereby altering the shape of the beam as it will reach the patient. Simultaneously with rotation of the gantry 24 about the patient, the couch 10 may be moved along a translation axis into or out of the treatment area (i.e. parallel to the axis of rotation of the chassis). With this simultaneous motion a helical radiation delivery pattern may be achieved.

The MRI apparatus 4, and specifically the signal-processing circuitry, may deliver real-time (or in practice near real-time) imaging data of the patient to the control circuitry. This information may allow the control circuitry to adapt the operation of the MLC 22, for example, such that the radiation delivered to the patient accurately tracks the motion of the target region, for example due to breathing, so that the radiation received by the patient is in accordance with a predetermined treatment plan contained within a treatment planning system, or TPS (not shown). All the control circuitry and the TPS may be integrated in one or more computer processors, so as collectively to ensure that the patient is treated in accordance with the predetermined plan.

Rotation of the gantry 24 can lead to changes in the relative alignment of components of the system. For example, small errors in control of the gantry rotation can accumulate and led to a mismatch between the assumed rotational position of the gantry and the actual rotational position. In another example, the alignment between the source 14 and the imaging device 26, or between the source 14 and the window 12 can vary due to small movements of the components. The net result of these changes can be that the beam delivered to the patient can vary from that assumed under the TPS.

One known method of checking gantry angle in a known radiotherapy system is to position a level check such as a spirit level on the gantry. However, the presence of the cryostat 9 makes this inconvenient in the embodiment shown in FIG. 1.

By utilizing static features of the system that appear in the image obtained by the imaging device 26, changes in the relative alignment of certain system components can be checked. For example, features of the MRI system 4 do not move and consequently the presence of these features in the images can act as spatial reference points against which relative movement of other components of the radiotherapy system 6 can be detected.

Figure 2:
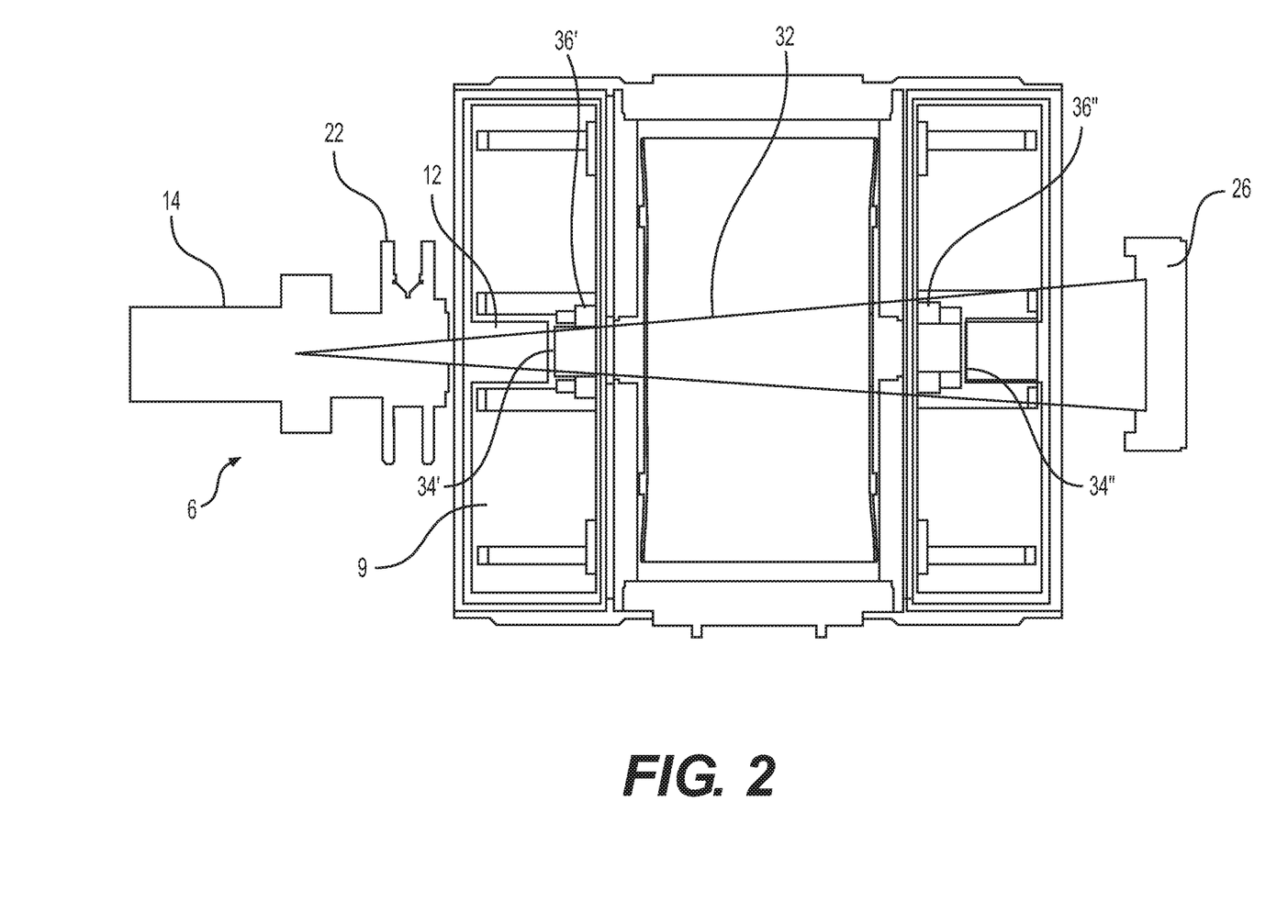
FIG. 2 shows a schematic section through the radiotherapy and MRI systems.

FIG. 2 shows a schematic section through the radiotherapy and MRI systems 6, 4, illustrating the manner in which the radiotherapy beam 32 interacts with the various features of the system 2.

In order to maintain fluid connection between the two halves of the cryostat 9, a balance pipe may be provided that extends across the window 12. The TPS may be programmed so as to account for the presence of the balance pipe in the beam when determining the dose to be provided to the patient. For example, the TPS may provide a beam shape and/or source control that avoids irradiating the balance pipe when delivering a treatment dose to the patient. While the balance pipe may not intersect the beam 32 when it is closest to the source 14 (position 34')r, the shape of the beam 32 means that the balance pipe on the opposite side (position 34") can intersect the beam 32, and appear in the image detected on the imaging device 26 as is described below.

The MRI system 4 may also include supports 36 for the coils of the primary magnet 8. Again, the supports closest to the source 14 (position 36') may not intersect the beam 32, but may appear on the opposite side (position 36").

As is known, the beam 32 may pass through the MLC 22, the leaves of which are positioned to define the shape of the beam at the isocenter.

By monitoring the position of features such as the balance pipe 34, coil supports 36, and leaves of the MLC 22, the relative alignment of the components of the system can be monitored.

Figure 3:
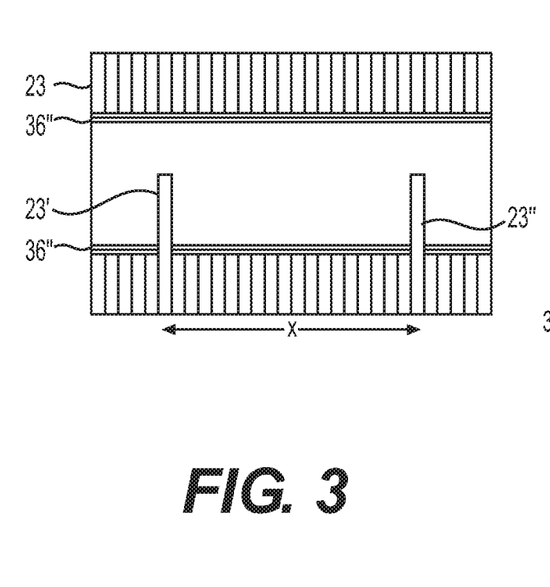
FIG. 3 shows the view through the multi-leaf collimator of the radiotherapy system towards the imaging system.
Figures 4, 5:
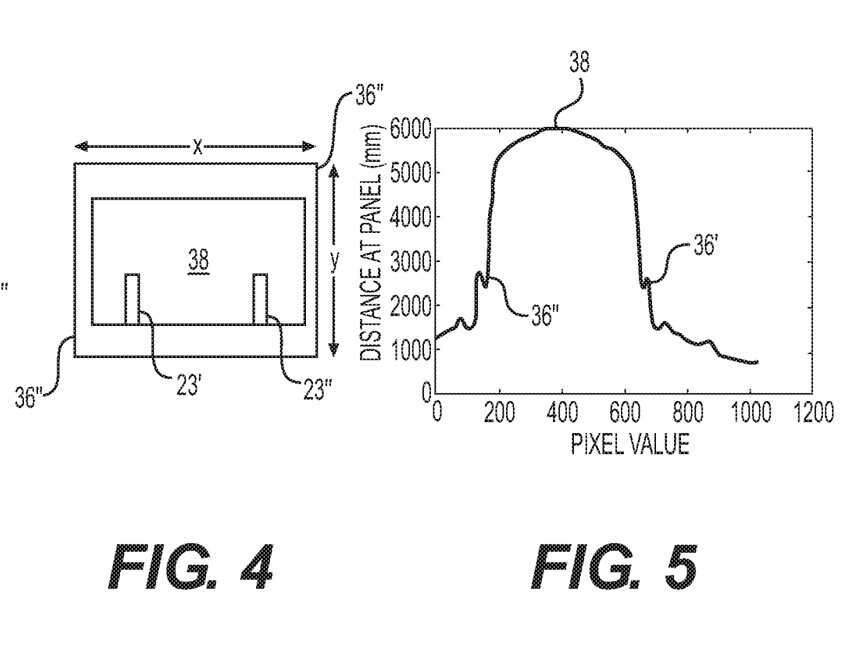
FIG. 4 shows the image obtained by the imaging system.
FIG. 5 shows the image signal across the image of FIG. 4 from top to bottom.

FIG. 3 shows the view through the MLC 22 towards the imaging system 26. All of the leaves 23 are fully retracted apart from two individual leaves 23', 23" close to the ends of the leaf array on one side. The edges of the supports 36" are visible through the gap of the MLC 22. FIG. 4 shows the image obtained by the imaging system 26 when the beam 32 is projected through the MLC 22 configured as shown in FIG. 3. The leaves 23', 23", and edges 36" are fully visible in the image. FIG. 5 shows the image signal across the image of FIG. 4 from top to bottom, i.e. edge 36" to edge 36" (not including the leaves 23', 23"). The centre of the image 38 shows a peak signal, and the edges 36" appear as smaller side peaks.

The MLC 22 may be securely fastened to the source 14 such that it does not move in use. Therefore, any movement of the position of the leaves 23', 23" in the x axis direction in successive images of FIG. 4 may be due to relative movement in the x axis direction of the source 14 and imaging system 26 (either the source 14 moves, the imaging system 26 moves, or both move in opposite directions). Similarly, any movement in the y axis direction of the edges 36" in successive images of FIG. 5 may be due to relative movement in the y axis direction of the source 14 and imaging system 26 (either the source 14 moves, the imaging system 26 moves, or both move in opposite directions).

In operation, an initial reference image can be taken when the original alignment of the system has been confirmed, and then subsequent images can be taken after periods of operation involving gantry rotation. The positions of the leaves 23 and edges 36 in the images can be monitored, and any changes in position can be used to indicate changes in alignment of the system components.

Figure 6:
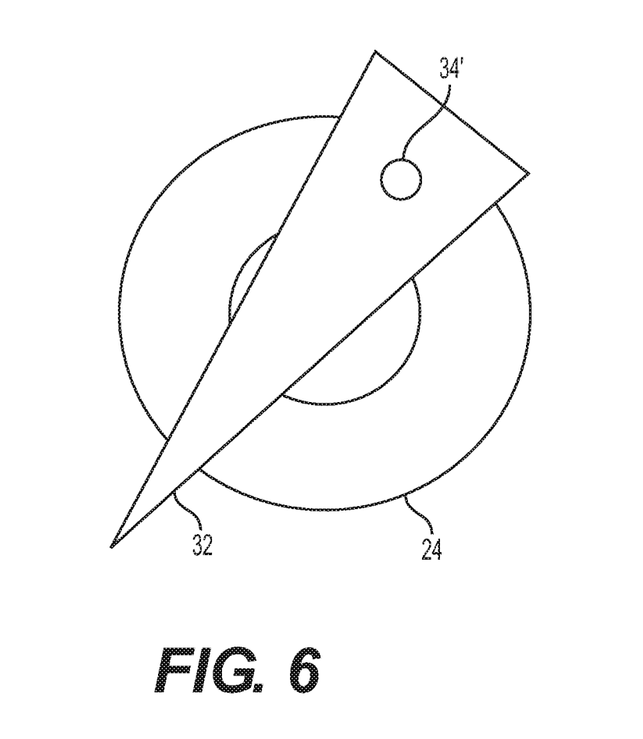
FIG. 6 shows a schematic diagram illustrating the position of the balance pipe in the beam.
Figure 7:
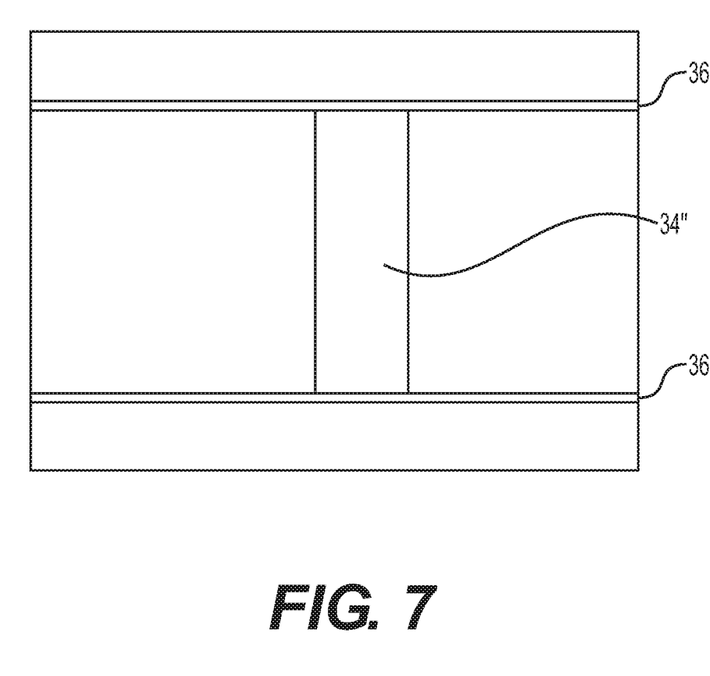
FIG. 7 shows the corresponding image obtained at the imaging system.

FIG. 6 shows a schematic diagram illustrating the position of the balance pipe 34 in the beam 32, and FIG. 7 shows the corresponding image obtained at the imaging system 26 where the balance pipe 34 appears in the beam when on the opposite side from the source. In this case, an initial image is taken with the gantry at a reference rotation angle with the balance pipe visible in the image. After operation of the system including rotation of the gantry, a control signal can be allied to reposition the gantry to the reference rotation angle and a further image taken. Movement of the position of the balance pipe 34 in the image indicates that the gantry has not returned to the original position indicating that the gantry calibration has drifted.

While a degree of relative movement might be acceptable without compromising the operation of the system, predetermined limits can be established to indicate when recalibration of the system is necessary.

Various changes can be made to the methods and systems disclosed above. While the system described above includes an MRI system, a part of which is the static component in the image, it will be appreciated that other components of a radiotherapy system can also provide the static component feature in the image that is used to determine relative movement of other parts of the system. Examples of other changes include the number and position of leaves of the MLC used for reference position can be adjusted to meet requirements. In addition, any other features of the MRI system that appear in the image can potentially be used for reference.

The invention claimed is:

1. A method of operating a radiotherapy system comprising a gantry rotatable around a treatment location, a radiotherapy beam generator located on the gantry, a radiotherapy imaging system located on the opposite side of the treatment location, and at least one component that is static with respect to the treatment location, wherein a beam path is defined between the radiotherapy beam generator and the radiotherapy imaging system so as to pass through the static component, the method comprising:

obtaining a reference image using the radiotherapy imaging system with the gantry in a predetermined position so as to provide the beam generator, the imaging system and the static component in reference positions, the reference image including the static component;

rotating the gantry relative to the static component;

returning the gantry to the predetermined position;

obtaining a second image using the radiotherapy imaging system with the gantry in the predetermined position, the second image including the static component; and determining changes in relative positions of the radiotherapy beam generator, the radiotherapy imaging system, and the static component based on differences in a position of the static component in the reference image and in the second image.

2. The method as claimed in claim 1, wherein:

the gantry is configured to surround a magnetic resonance imaging system, wherein the static component is a predetermined feature of the magnetic resonance imaging system;

the radiotherapy beam generator is located on one side of the magnetic resonance imaging system;

the radiotherapy imaging system is located on the opposite side of the magnetic resonance imaging system;

the beam path is defined between the radiotherapy beam generator and the radiotherapy imaging system so as to pass through the magnetic resonance imaging system;

the gantry is configured to rotate the radiotherapy beam generator around the magnetic resonance imaging system; and wherein the method further comprises:

obtaining the reference image using the radiotherapy imaging system, the reference image including the predetermined feature of the magnetic resonance imaging system located near the radiotherapy imaging system;

rotating the radiotherapy system relative to the magnetic resonance imaging system;

obtaining the second image using the radiotherapy imaging system, the second image including the predetermined feature of the magnetic resonance imaging system located near the radiotherapy imaging system; and determining changes in relative positions of the radiotherapy beam generator, the radiotherapy imaging system, and the magnetic resonance imaging system based on differences in a position of the predetermined feature in the reference image and in the second image.

3. The method as claimed in claim 2, further comprising, determining a degree of rotation to rotate the gantry to a position at which the reference image was obtained;

providing a control signal for the gantry to rotate through the degree of rotation;

obtaining the reference image; and determining an error in a rotational position of the gantry based on changes in a relative position of the predetermined feature in the reference and second images.

4. The method as claimed in claim 2, wherein the predetermined feature includes at least one of a part of a cryostat or a part of a coil support of the magnetic resonance imaging system.

5. The method as claimed in claim 4, wherein the beam path extends through a gap provided in at least one of the cryostat or the coil support.

6. The method as claimed in claim 5, wherein the predetermined feature in the reference image includes edges of the gap.

7. The method as claimed in claim 5, wherein the predetermined feature in the reference image includes edges of the gap and features of a collimation system located between the beam generator and the radiotherapy imaging system.

8. The method as claimed in claim 2, wherein the reference image includes features of a collimation system located between the beam generator and the magnetic resonance imaging system.

9. The method as claimed in claim 8, wherein the features of the collimation system include one or more leaves of a multi-leaf collimator.

10. A radiotherapy system comprising:
a gantry rotatable around a treatment location;
a radiotherapy beam generator located on the gantry;
a radiotherapy imaging system located on the opposite side of the treatment location; and
at least one component that is static with respect to the treatment location, wherein:
a beam path is defined between the radiotherapy beam generator and the radiotherapy imaging system so as to pass through the static component;
the radiotherapy imaging system is configured to obtain a reference image with the gantry in a predetermined position so as to provide the beam generator, the imaging system and the static component being in reference positions, and the reference image including the static component;
the gantry is configured to rotate relative to the static component and return to the predetermined position;
the radiotherapy imaging system is configured to obtain a second image with the gantry in the predetermined position, the second image including the static component; and
changes in relative positions of the radiotherapy beam generator, the radiotherapy imaging system, and the static component are configured to be determined based on differences in a position of the static component in the reference image and in the second image.

11. The system as claimed in claim 10, further comprising:
a magnetic resonance imaging system, wherein the gantry is configured to surround the magnetic resonance imaging system;
the radiotherapy beam generator located on one side of the magnetic resonance imaging system; and
the radiotherapy imaging system located on the opposite side of the magnetic resonance imaging system, wherein:
the beam path is defined between the radiotherapy beam generator and the radiotherapy imaging system so as to pass through the magnetic resonance imaging system;
the gantry is arranged to rotate the radiotherapy beam generator around the magnetic resonance imaging system;
the radiotherapy imaging system is configured to obtain the reference image, the reference image including as the static component, a predetermined feature of the magnetic resonance imaging system located near the radiotherapy imaging system;
the gantry is configured to be rotated relative to the magnetic resonance imaging system;
the radiotherapy imaging system is configured to obtain the second image, the second further image including the predetermined feature of the magnetic resonance imaging system located near the radiotherapy imaging system; and
changes in relative positions of the radiotherapy beam generator, the radiotherapy imaging system, and the magnetic resonance imaging system are configured to be determined based on differences in a position of the predetermined feature in the reference image and in the second image.

12. The system as claimed in claim 11, wherein the predetermined feature includes at least one of a part of a cryostat or a part of a coil support of the magnetic resonance imaging system.

13. The system as claimed in claim 12, wherein the beam path extends through a gap provided in at least one of the cryostat or the coil support.

14. The system as claimed in claim 13, wherein the predetermined feature in the reference image includes edges of the gap.

15. The system as claimed in claim 13, wherein the predetermined feature in the reference image includes edges of the gap and features of a collimation system located between the beam generator and the radiotherapy imaging system.

16. The system as claimed in claim 11, wherein the reference image includes features of a collimation system located between the beam generator and the magnetic resonance imaging system.

17. The system as claimed in claim 16, wherein the features of the collimation system include one or more leaves of a multi-leaf collimator.

18. A non-transitory computer-readable medium comprising instructions that, when executed by at least one processor, cause the at least one processor to perform operations, comprising:
obtaining a reference image using a radiotherapy imaging system with a gantry in a predetermined position so as to provide a beam generator, wherein:
the gantry is rotatable around a treatment location;
the imaging system is located on the opposite side of the treatment location;
at least one component is static with respect to the treatment location;
a beam path is defined between the radiotherapy beam generator and the radiotherapy imaging system so as to pass through the static component;
the imaging system and the static component are in reference positions; and
the reference image includes the static component;
rotating the gantry relative to the static component;
returning the gantry to the predetermined position;
obtaining a second image using the radiotherapy imaging system with the gantry in the predetermined position, the second image including the static component; and
determining changes in relative positions of the radiotherapy beam generator, the radiotherapy imaging system, and the static component based on differences in a position of the static component in the reference image and in the second image.

19. The non-transitory computer-readable medium as claimed in claim 18, wherein:
- the gantry is configured to surround a magnetic resonance imaging system;
- the static component is a predetermined feature of the magnetic resonance imaging system;
- the radiotherapy beam generator is located on one side of the magnetic resonance imaging system;
- the radiotherapy imaging system is located on the opposite side of the magnetic resonance imaging system;
- the beam path is defined between the radiotherapy beam generator and the radiotherapy imaging system so as to pass through the magnetic resonance imaging system;
- the gantry is configured to rotate the radiotherapy beam generator around the magnetic resonance imaging system; and
- the operations further comprise:
  - obtaining the reference image using the radiotherapy imaging system, the reference image including the predetermined feature of the magnetic resonance imaging system located near the radiotherapy imaging system;
  - rotating the radiotherapy system relative to the magnetic resonance imaging system;
  - obtaining the second image using the radiotherapy imaging system, the second image including the predetermined feature of the magnetic resonance imaging system located near the radiotherapy imaging system; and
  - determining changes in relative positions of the radiotherapy beam generator, the radiotherapy imaging system, and the magnetic resonance imaging system based on differences in a position of the predetermined feature in the reference image and in the second image.

20. The non-transitory computer-readable medium as claimed in claim 19, wherein the operations further comprise:
- determining a degree of rotation to rotate the gantry to a position at which the reference image was obtained;
- providing a control signal for the gantry to rotate through the degree of rotation;
- obtaining the reference image; and
- determining an error in a rotational position of the gantry based on changes in a relative position of the predetermined feature in the reference and second images.

* * * * *